United States Patent [19]

Zebehazy

[11] Plant 5,195

[45] Feb. 28, 1984

[54] LEUCOTHOE PLANT-ZEBLID VARIETY

[75] Inventor: Alex J. Zebehazy, Perry, Ohio

[73] Assignee: The Conard-Pyle Company, West Grove, Pa.

[21] Appl. No.: 161,870

[22] Filed: Jun. 23, 1980

[51] Int. Cl.[3] ..... A01H 5/00

[52] U.S. Cl. ..... Plt./54

[58] Field of Search ..... Plt./54

*Primary Examiner*—James R. Feyrer

*Attorney, Agent, or Firm*—Burns, Doane, Swecker & Mathis

[57] ABSTRACT

A new and distinct variety of Leucothoe is provided. While the new variety is believed to have originated as a cross-pollination of *Leucothoe fontanesiana* with pollen from *Leucothoe axillaris,* this cross cannot be confirmed. The new variety exhibits a highly attractive leaf coloration as well as outstanding tolerance to shade, and is very hardy.

3 Drawing Figures

SUMMARY OF THE INVENTION

My invention relates to a new, distinctive and useful form of Leucothoe plant which was originated by me at Perry, Ohio. A breeding program was carried out whereby plants of *Leucothoe fontanesiana* were pollinated with pollen from plants which were purchased as being *Leucothoe axillaris.* However, there is the possibility that the pollen parent may have actually been *Leucothoe fontanesiana* var. nana. Also, following the attempted pollen transfer, the flowers of the seed parent were not bagged thereby making possible the introduction of pollen from an unknown source.

The object of my breeding was to create a colorful new variety of Leucothoe which combined the hardiness of *Leucothoe fontanesiana* with the attractive dwarf growth habit of *Leucothoe axillaris,* and which exhibited improved foliage coloration over both parents. This objective was achieved, along with other improvements, and the new variety exhibits a combination of characteristics which distinguish it from all other forms of Leucothoe of which I am aware.

The following combination of characteristics is exhibited by the new variety:

(a) a dense, compact, and symmetrical habit of growth which is much more attractive and compact than the *Leucothoe fontanesiana* parent, (b) striking scarlet coloration of the new growth during the growing season, which is virtually never found in either parent, (c) highly unique winter coloration which ranges from a greenish bronze to scarlet, making the new variety an outstanding source of color in the landscape throughout the year, (d) outstanding tolerance to shade, making the variety an important addition to that small group of plants that do well in diminished sunlight, (e) substantial absence of dead branches, which are commonly found with *Leucothoe fontanesiana,* and (f) increased tolerance to cold when compared to *Leucothoe axillaris,* as is evidenced by the fact that the variety when established has survived temperatures of −15° F. with little to no damage, whereas *Leucothoe axillaris* is listed as hardy to 0° F.

In excess of fifty percent of two year old container grown plants of the present variety measure approximately 12 to 15 inches in breadth when grown at West Grove, Pa.

Asexual reproduction of my new variety by cuttings has been accomplished at Perry, Ohio, and West Grove, Pa. Succeeding propagations have shown that the unique combination of characteristics is fully established and transmitted to successive generations.

The new variety has been named the Zeblid variety.

BRIEF DESCRIPTION OF THE PHOTOGRAPHS

The accompanying photographs show typical specimens of my new variety of Leucothoe as depicted in color as true as is reasonably possible to make the same in color photographs of this character. The specimens in the photographs were grown in the ground at West Grove, Pa.

DETAILED DESCRIPTION

Figure 1:
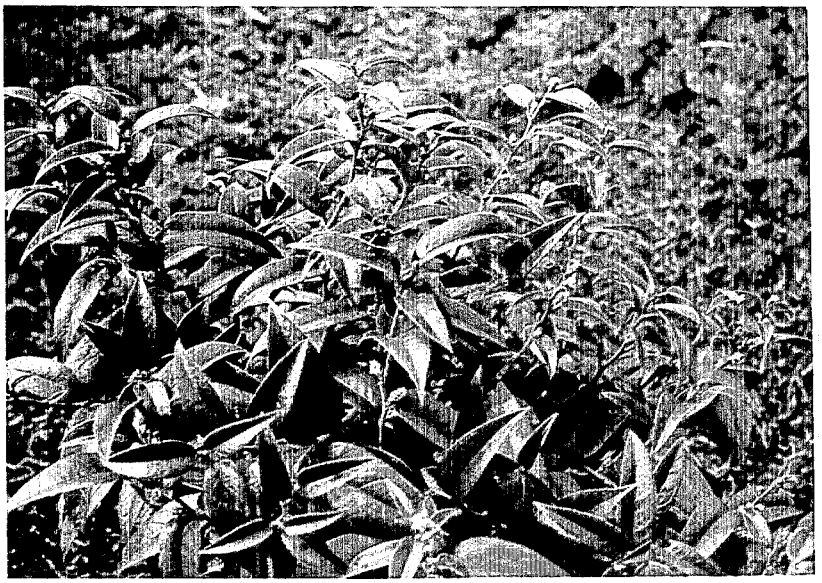
FIG. 1 shows a typical three year old plant of the present variety during early spring prior to the formation of young shoots.
Figure 2:
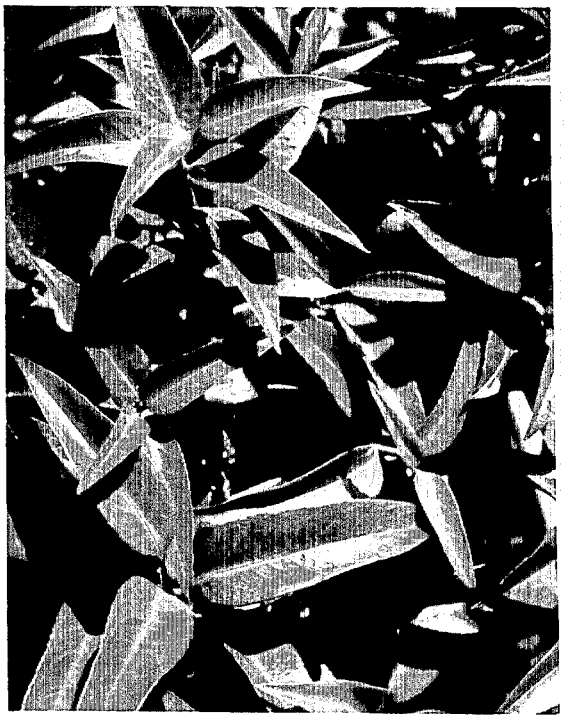
FIG. 2 shows the typical scarlet coloration of newly formed young shoots during early summer.
Figure 3:
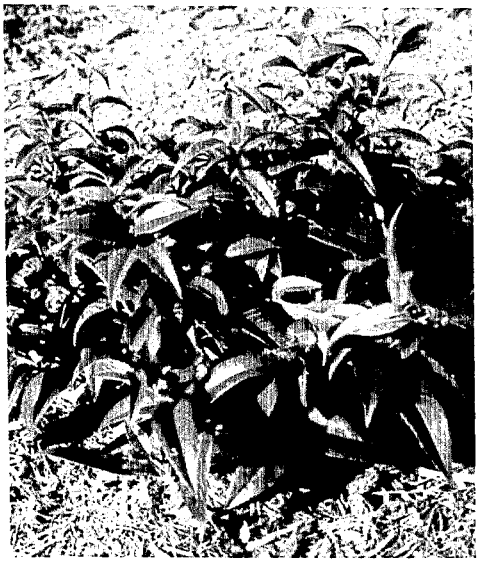
FIG. 3 shows the typical appearance of a three year old plant during the winter.

The following is a detailed description of my new variety made from three year old plants growing in the ground at West Grove, Pa. Color terminology is in accordance with the R.H.S. Colour Chart of The Royal Horticultural Society, London, England.

Parentage: *Leucothoe fontanesian* × *Leucothoe axillaris.*

Foliage:

*Type.*—Evergreen. Leaves lanceolate, apex slightly acuminate, base obtuse. Margins serrulate.

*Size of mature leaves.*—From approximately 5.9 to 9.9 cm. in length, with an average of approximately 7.8 cm.; from approximately 2.4 to 3.6 cm. in width, with an average of approximately 3.2 cm. Petiole length from approximately 0.6 to 1.0 cm.

*Color.*—Mature leaves in May, upper surface — Green Group 139A; under surface — closest to Green Group 137D.

*Fully expanded immature leaves in May, upper surface.*—Slightly darker than Yellow Green Group 144A; under surface — Yellow Green Group 146D. The immature leaves have a slight crimson cast to their margins.

*Young shoots in May.*—Slightly yellower than Greyed Purple Group 183B.

*Leaves in January.*—From Greyed Red Group 178A to 178C.

*Petiole color.*—Red-Purple Group 60A.

Flowers: Flowers appear in May and are substantially identical to flowers of the *axillaris* and *fontanesiana* species.

I claim:

1. A new and distinct variety of Leucothoe, substantially as herein shown and described, characterized particularly as to novelty by the unique combination of:

(a) a dense, compact, and symmetrical habit of growth which is much more attractive and compact than the *Leucothoe fontanesiana* parent, (b) striking scarlet coloration of the new growth during the growing season, which is virtually never found in either parent, (c) highly unique winter coloration which ranges from a greenish bronze to scarlet, making the new variety an outstanding source of color in the landscape throughout the year, (d) outstanding tolerance to shade, making the variety an important addition to that small group of plants that do well in diminished sunlight, (e) substantial absence of dead branches, which are commonly found with *Leucothoe fontanesiana,* and (f) increased tolerance to cold when compared to *Leucothoe axillaris,* as is evidenced by the fact that the variety when established has survived temperatures of −15° F. with little to no damage, whereas *Leucothoe axillaris* is listed as hardy to 0° F.

* * * * *